(12) United States Patent
Charles et al.

(10) Patent No.: US 6,656,478 B1
(45) Date of Patent: Dec. 2, 2003

(54) CROSS-PROTECTIVE SALMONELLA VACCINES

(76) Inventors: Samuel D. Charles, Bayer Corporation, 100 Bayer Rd., Pittsburgh, PA (US) 15205-9741; Albert Surendran Abraham, Bayer Corporation, 100 Bayer Rd., Pittsburgh, PA (US) 15205-9741; Emilio Trigo-Tavera, Bayer Corporation, 100 Bayer Rd., Pittsburgh, PA (US) 15205-9741

( * ) Notice: Subject to any disclaimer, the term of this patent is extended or adjusted under 35 U.S.C. 154(b) by 0 days.

(21) Appl. No.: 09/439,589

(22) Filed: Nov. 12, 1999

(51) Int. Cl.[7] .............................................. A61K 39/112
(52) U.S. Cl. ................ 424/258.1; 424/234.1; 424/235.1; 435/172.1; 435/243
(58) Field of Search .......................... 424/235.1, 234.1, 424/258.1; 435/172.1, 243

(56) References Cited

U.S. PATENT DOCUMENTS 5,436,001 A * 7/1995 Kramer
5,468,485 A * 11/1995 Curtiss, III

OTHER PUBLICATIONS

Stabel et al. Infection & Immunity. 61(2): 610–618, 1993.*
Fox et al. AJVR. 58(3): 265–271, Mar. 1997.*
Animal Pharm. Mar. 20, 1998. 393: 21. (abstract citation only), Mar. 20, 1998.*
Newell et al, J.A.V.M.A. 158/1:89–98, 1971.*
Reed et al, Am. J. Vet. Res. 47/1:75–83, 1986.*
Nnalue et al, Infection & Immunity 55/4:955–62, 1987.*
Stabel et al, Infection & Immmunity 61/2:610–618, 1993.*
Lax et al, Br. Vet. J. 151:351–377, 1995.*
Am. J. Vet. Res., vol. 45, Sep., 1984, pp. 1858–1861, Bradford P. Smith et al, "Vaccination of Calves Against Salmonella Dublin With Aromatic–Dependent Salmonella Typhimurium".
Am. J. Vet. Re., vol. 45, Nov., 1984, pp. 2231–2235, Bradford P. Smith et al, "Aromatic–Dependent Salmonella Dublin As A Parenteral Modified Live Vaccine For Calves"
ISECSP: Production Intervention, (month unavailable), 1999, pp. 321–325, A. Letellier et al, "Assessment of Different Treatments To Reduce Salmonella In Swine".
ISECSP: Production Intervention, (month unavailable), 1999, pp. 317–320, A. Letellier et al "Host Response To Different Treatments To Reduce Salmonella Infections In Swine".

* cited by examiner

Primary Examiner—Jennifer E. Graser
(74) Attorney, Agent, or Firm—William M. Blackstone

(57) ABSTRACT

The present invention relates to a method of protecting pigs against disease caused by infection by heterologous serotypes of Salmonella including but not limited to *S. typhimurium* comprising administering to the pigs a modified live vaccine incorporating *S. cholerasuis*.

3 Claims, No Drawings

CROSS-PROTECTIVE SALMONELLA VACCINES

BACKGROUND OF THE INVENTION

The present invention relates to salmonella vaccines that are useful against Salmonellosis caused by heterologous serotypes of Salmonella in mammals. More specifically, the invention relates to salmonella vaccines for swine incorporating *Salmonella cholerasuis* which provides cross protection against disease caused by heterologous Salmonella species including but not limited to *Salmonella typhimurium*.

BRIEF DESCRIPTION OF THE PRIOR ART

Salmonellosis of swine is one of the most economically important of the enteric and septicemic diseases affecting young pigs. Although many serotypes of Salmonella have been isolated from pigs, *S. cholerasuis* var kunzendorf and *S. typhimurium* are the two most frequently isolated serotypes associated with clinical disease. *S. cholerasuis* is host-adapted to swine and most often causes fatal septicemic disease with little involvement of the intestinal tract. On the other hand, *S. typhimurium* typically causes enteroinvasive disease characterized primarily or exclusively by diarrhea. The initial signs of the disease include watery, yellowish diarrhea without mucin or melena. Affected pigs often exhibit anorexia, lethargy, and fever ranging from 105 to 107 degrees Fahrenheit. Mortality is usually low and occurs only after several days of diarrhea, presumably the result of hypokalemia and dehydration. Literature clearly notes that both the type of infection and host range vary significantly between *S. cholerasuis* and *S. typhimurium*.

It has been known to use *Salmonella cholerasuis* vaccines such ARGUS SC™ vaccine (Intervet Inc., Millsboro, Del.) to protect pigs against diseases caused by infection from *S. cholerasuis* (homologous protection). The vaccine of the present invention incorporates a modified live *S. cholerasuis*, the composition of which is described generally in U.S. Pat. No. 5,468,485. More specifically, the patent discloses a vaccine for the immunization of vertebrates or invertebrates comprising an avirulent derivative of *S. cholerasuis*. The derivative is substantially incapable of producing functional adenylate cyclase (cya gene deletion) and/or cyclic AMP receptor protein (crp). The patent also discloses a vaccine for immunization of a vertebrate or invertebrate comprising a virulent derivative of a pathogenic microbe, which is substantially incapable of producing functional adenylate cyclase and/or cyclic AMP receptor protein. Said pathogenic microbe is capable of expressing a recombinant gene derived from a pathogen of said vertebrate to produce an antigen capable of inducing an immune response in said vertebrate against said pathogen. This patent describes construction of various avirulent Salmonella species but does not disclose or claim use of a *S. cholerasuis* vaccine to protect pigs against disease caused by a heterologous Salmonella such as *S. typhimuirum*.

U.S. Pat. No. 5,804,194 discloses vaccines containing Salmonella bacteria attenuated by mutation of the HTRA gene. This mutation also produces avirulent salmonella vaccines which appear to be safe when injected into mice. Also described is vaccination of mice by a vaccine of the invention followed by challenge with a homologous *S. typhimurium* strain. There is no description or claim of a *S. cholerasuis* vaccine having the capability to cross protect against diseases caused by heterologous Salmonella species.

U.S. Pat. No. 5,843,426 discloses salmonella vaccines containing salmonella organisms, the virulence of which is attenuated by a deletion of a portion of the PhQ gene and Salmonella organisms having a deletion of both the PhQ gene and the PhoP gene. There is no mention of a *S. cholerasuis* vaccine which can cross protect pigs against disease caused by heterologous Salmonella species.

Miller et al., 1989, Proc. Natl. Acad. Sci USA 86:5054 discloses *S. typhimurium* strains with mutations in the positive regulatory regulon phoP which are markedly attenuated in virulence for BALB C mice. The phoP regulon is composed of two genes present in an operon termed phoP and phoQ. The PhoP and the phoQ gene products are highly similar to other members of bacterial two-component transcriptional regulators that respond to environmental stimuli and control the expression of a large number of other genes. A mutation at one of these PhoP regulatory regions, regulates the pagC genes and produces a virulence defect. Strains with pagC, phoP and phoQ mutations afford partial protection to subsequent challenge by wild-type *S. typhimurium*. However, there is no description or claim made for *S. cholerasuis* vaccines which cross protect against diseases caused by heterologous Salmonella species.

U.S. Pat. No. 5,436,001 discloses methods of attenuating virulent Gram negative bacteria in order to produce avirulent vaccine strains. The method is described as serial passaging a gram negative organism through phagocytic cells a sufficient number of times until the bacteria are rendered avirulent to the animal host while still being immunogenic. A method to attenuate *S. cholerasuis* var, Kunzendorf strain 38 is described. Several pig vaccination/challenge studies were conducted. These studies demonstrated that a *S. cholerasuis* attenuated, and produced according to the methods of the patent, could protect against a homologous S. cholerasuis challenge. However, there was no description or claim of cross protection using a *S. cholerasuis* vaccine to protect against disease caused by a heterologous Salmonella such as *S. typhimurium*.

Smith et al (Am J Vet Res, 1984, Vol 45, No. 11: 2231–2235) describes an aromatic-dependent avirulent *S. dublin* strain which was tested for safety as a parenteral vaccine for calves as well as for its capability to protect calves from challenge with homologous *S. dublin* or heterologous *S. typhimurium*. Indeed, the vaccine was shown to be safe and provided protection against disease in cattle caused by both *S. dublin* and *S. typhimurium*. However, the publication states that in a previous study, conducted in an identical manner, protection was not produced. Additionally, it is noted that this publication does not describe the use of *S. cholerasuis* vaccines to cross protect against disease caused by eterologous Salmonella of swine nor does it describe oral vaccination.

Alternately, Smith et al (Am J Vet Res, 1984, Vol 45, No 11: 858–1861) describe the production of an aromatic-dependent avirulent *S. typhimurium* which was tested for safety and efficacy in calves. Both the ability to protect against a homologous *S. typhimurium* challenge and a heterologous *S. dublin* challenge were evaluated. The parental vaccine was found to be relatively safe although some disease signs were noted post vaccination. Since 2 of 5 vaccinated calves had slight anorexia, 4 of 5 had diarrhea, and all had marked febrile response after challenge exposure, it was determined that the aromatic-dependent avirulent *S. typhimurium* vaccine did not protect calves against a different serotype (*S. dublin*) as well as it had against a homologous serotype (*S. typhimurium*). However, even against the homologous challenge, 3 of 7 vaccinated calves developed mild diarrhea and 1 of 7 calves had a positive blood culture. This publication actually teaches away from the present invention of a *S. cholerasuis* vaccine which cross protects against disease caused by a heterologous Salmonella species such as *S. typhimurium*.

Fox et al (Am J Vet Res, 1997, Vol 58, No. 3, 265–271) describes an attempt to use an avirulent live *S. cholerasuis* vaccine to protect calves against disease caused by *S. dublin* infection. The vaccine, designated SC54, contains an avirulent live culture of *S. cholerasuis* normally used for intranasal or oral vaccination of swine to aid in the prevention of salmonellosis in swine caused by *S. cholerasuis*. The results indicate a varied response to vaccination of calves with different doses and routes of administration of SC54. Vaccination with SC54 did not prevent the fever and fecal shedding of *S. dublin* but did reduce the bacteremia and frequency of *S. dublin* recovery from organs of calves at necropsy when vaccine was administered intranasally. The conclusion was that SC54 appears to have potential as a safe and effective vaccine against disease in calves caused by *S. dublin*. However, its efficacy against *S. typhimurium* infection in calves was not demonstrated. This publication teaches away from use of a *S. cholerasuis* vaccine for cross protection of swine against disease caused by a heterologous Salmonella species such as *S. typhimurium.*

Letellier et al (1999 ISECSP: Production Intervention) has described the evaluation of different treatments to reduce Salmonella infections in swine. These treatments include *Salmonella cholerasuis* vaccines FOS (1% in feed, Encore Technologies), FERLAC-2™ in feed, (Rosell Institute, Montreal Canada) and intranasal vaccination with SC54™ (Boehringer Ingleheim, Iowa). The publication indicates that the colonization of mesenteric lymph nodes for SC54™ vaccinated pigs was reduced in comparison to the control group. There was also a reduction in prevalence of Salmonella in the ileum. However, there was no difference observed in quantitative evaluation of *S. typhimurium* in the mesenteric lymph nodes. Also, phagocytosis from whole blood phagocytes was not increased after treatments suggesting that systemic stimulation of phagocytes was not sufficient to increase resistance to *S. typhimurium*. This publication, although testing an avirulent *S. cholerasuis* vaccine for cross protection in pigs was not successful in demonstrating such cross protection. It teaches away from the present invention.

Letellier et al (1999 ISECSP: Production Intervention) reported on the Assessment of different treatments to reduce Salmonella in swine. In this study, SC54™ was again evaluated for potential cross protection of swine against disease caused by hetero-logous Salmonella. Following experimental infection with *S. typhimurium*, 70% of the control pigs became colonized by *S. typhimurium* in the gut and 60% were infected in mesenteric lymph nodes. No significant difference was observed in quantitative evaluation of *S. typhimurium* in the mesenteric lymph nodes in the different groups (including the SC54™ group). SC54™ did reduce the presence of *S. typhimurium* in the mesenteric lymph nodes but it did not reduce shedding of *S. typhimurium* in feces. In fact, there was an increase in the fecal shedding in the vaccinate group as compared with the control group. This publication does not present conclusive evidence and does not teach cross protection of heterologous Salmonella by vaccination with a *S. cholerasuis* vaccine.

While it has been generally known that there can be cross reactivity (immunological tests indicate that antibodies of one serotype of Salmonella react with other serotypes of Salmonella), cross protection between Salmonella serotypes (heterologous protection) has been poorly characterized and unproven. These showings are insufficient for making and using salmonella vaccines incorporating one serotype to provide protection in swine against another. Certainly, the use *S. cholerasuis* vaccine which is typically useful in protecting pigs against septicemia and death would not be expected to protect against *S. typhimurium* which produces a severe diarrhea in all mammals.

By this invention, Applicant has provided an avirulent *S. cholerasuis* vaccine, which can cross protect against disease caused by infection with heterologous Salmonella serotypes such as *S. typhimurium.*

DESCRIPTION OF THE INVENTION

As set forth above, the present invention relates to a method of protecting pigs against disease caused by infection with heterologous serotypes of Salmonella (cross protection) including but not limited to *S. typhimurium* comprising administering to the pigs a modified live vaccine incorporating *S. cholerasuis*. It is a distinct feature of the invention that the vaccine can be administered orally or parenterally. It is also a distinct feature that the vaccine can be mass delivered in drinking water.

The avirulent *S. cholerasuis* vaccine of the present invention comprises a *S. cholerasuis* strain $\chi$3781 (Δ cya Δ(crp-cdt) which is a mutant with portions of the genes encoding adenylate cyclase (cya), cAMP receptor protein (crp) and the ability to colonize deep tissue (cdt) modified by transposon mutagenesis. In addition, the organism contains an auxotrophic requirement for methionine. Therefore, the production of the vaccine requires that the *S. cholerasuis* avirulent strain be grown on media supplemented with methionine. After growing to an optimum optical density or to a count (colony forming units) $>2\times10^8$ the culture is harvested, stabilizer is added and the stabilized culture is filled into final containers and lyophilized (freeze-dried). Stabilizers can be of any type including but not limited to sucrose, gelatin, skim milk, dextrose, Lactalbumin Hydrolysate, NZ amine, Glutamic Acid and combinations thereof. A preferred stabilizer is a combination of 3.0% NZ-amine Type AS, 0.3% Glutamic Acid, monopotassium salt, 25% sucrose, 0.2% Lactalbumin Hydrolysate (Edamin S) and 5.0% Gelatin. At the time of use, diluent is added to the lyophilized final product container to resuspend the *S. cholerasuis* modified live vaccine and the vaccine is administered to pigs. Administration can be 1.0 mL delivered parenterally to pigs (subcutaneously, intramuscularly or intraperitoneally), 1.0 mL delivered to a mucous membrane such as into the mouth, eye, vagina, or rectum, or preferably, addition of 1.0 mL per pig to a water proportioner such that pigs will drink the water and be vaccinated simultaneously. The specific vaccine of the present invention, Argus SC™, is used as an aid in prevention of pneumonia, diarrhea, septicemia and mortality caused by *S. cholerasuis* in pigs 3 weeks of age or older.

As would be realized from the foregoing, it will be within the purview of the skilled artisan to make and use a modified live *S. cholerasuis* vaccine such as Argus SC™. The *S. cholerasuis* is grown in a media selected for optimization of the production of immunogenic avirulent organisms. Optimal growth of *S. cholerasuis* strain $\chi$3781 (Δ cya Δ(crp-cdt) is reached when the culture demonstrates an optical density of 2.5 at 600 nm. This equates to approximately $2\times10^{8}$ CFU/mL. However, a dose as low as $1\times10^5$ has been shown to be effective. The preferred dose is at least $1\times10^7$ CFU/mL. The term immunogenic avirulent organisms means that the organisms will not produce disease when administered to pigs (they are safe) and that when the organisms are formulated into a vaccine, the vaccine will cross protect swine from diseases caused by homologous and heterologous serotypes of Salmonella including but not limited to S. typhimurium. After growth of the S. cholerasuis it is generally mixed with a stabilizer selected from the group consisting of NZ-amine, Glutamic Acid, Sucrose, Lactalbumin hydrolysate, gelatin, other stabilizing sugars and combinations thereof and then dried. Drying can be accomplished by lyophilization (freeze-drying), vitrification, glassification, or any other method which retains the viability of the organisms. The vaccine can be administered by any route selected from the group consisting of oral, drinking water, intranasal, intramucosal, intramuscular, subcutaneous, intravenous and intraperitoneal. The preferred route is oral or intranasal via drinking water.

The above disclosure generally describes the present invention. A more complete understanding can be obtained by reference to the following specific examples which are provided herein for purposes of illustration only and are not intended to be limiting unless otherwise specified.

EXAMPLE 1

This study was conducted in order to determine whether a *S. cholerasuis* vaccine, specifically Argus SC™, could cross protect pigs from disease caused by a heterologous serotype of Salmonella, *S. typhimurium*. In this study, 69 three to four week old crossbred pigs (female and male) which were negative for Salmonella were weighed and randomly assigned to four groups. The vaccine was orally mass administered using a water proportioner. Group I received Argus SC™ containing $5\times10^7$ CFU/pig while Group II received $1\times10^8$ CFU/pig. The pigs in Group III were not vaccinated but were challenged (Controls) and pigs in Group IV were not vaccinated or challenged (sentinels). The protocol and criteria for evaluation of protection were as follows: "Baseline" values on physical condition, fecal consistency body weight and rectal temperature were determined for each pig on various days during a three day pre-vaccination period (Days 1 to 5). On Day 6, the pigs from Groups I and II were vaccinated. Three weeks post vaccination (Day 27), pigs from Groups I, II, and III were orally challenged with a virulent strain of *S. typhimurium*. Prior to challenge, physical condition, fecal consistency, rectal temperature, and body weight were determined for each animal on Days 25 through 27. During the 14-day post challenge period, efficacy of the vaccines was assessed by evaluating the physical condition (morbidity scores), fecal condition (diarrhea scores), rectal temperature, body weight and mortality. Animals that died during the post challenge period were subjected to necropsy. At the end of the observation period (Day 41), the body weight for each pig was recorded and the experiment was terminated.

The protocol and criteria for this study were as follows:

Prior to vaccination, water was withdrawn from the pigs for a period of six hours. Three weeks post-vaccination (Day 27), animals of Group I and Group II were challenged orally with a virulent strain of *Salmonella typhimurium*, P93-482. Prior to challenge, "baseline" values on physical condition, fecal consistency, rectal temperature and body weight were determined for each animal. Before challenge, feed was withdrawn from the pigs for 16 hours. Feed was returned to the pigs after 30 minutes of challenge-exposure. Fourteen days post-challenge, efficacy of the vaccine was assessed by evaluating the physical condition and fecal consistency scores, rectal temperature, and average daily gain (ADG) on various days during the post-challenge Days 29 to 41.

The challenge culture was prepared by removing a frozen vial of *S. typhimurium* and thaw it in a 37° C. water bath. Aliquots (1 mL) of the thawed culture were transferred to two 2 L Erlenmeyer flasks, each of which contained 500 mL of MLB (Modified Luria Bertani) broth (10 g Bacto tryptone, 5 g yeast extract, and 10 g NaCl per liter of deionized water).

After 14 to 16 hours of static growth at 37° C.±2° C., the two cultures were combined to obtain a total volume of approximately one-liter. Aliquots (100 mL) were dispensed into sterile bottles and stored in an ice-water bath until administered to the pigs, within one hour of standardization. A viable bacterial count was conducted on the challenge culture and indicated that each pig received a challenge containing $1\times10^{10}$ colony forming units (CFU). Each pig was restrained and orally given an oral challenge of the *S. typhimurium* culture using a plastic syringe.

For sampling and data collection, each pig was assigned to a clinical chart on which clinical observations and sampling were recorded. Mortality was scored throughout the entire study period. Fecal consistency and physical condition were evaluated daily for each pig.

Fecal consistency was scored as:

1=Normal, solid or soft-formed

2=Runny, with solid material

3=Watery, with solid material

4=Profuse watery with little or no solid material.

The mean value of stool scores for the 14 day post-challenge observation period was converted to a "percent diarrhea" by subtracting the corresponding "baseline" value (average for the pre-challenge period [1.00]) from the mean post-challenge score. The difference was then divided by the adjusted maximum possible score (4.0−1.0=3.00), and multiplied by 100.

Physical condition (morbidity) of the pigs was scored as:

1=Healthy, active, with a normal hair-coat

2=Slightly active, with a rough hair-coat

3=Inactive/lethargic and/or gaunt irrespective of hair-coat

4=Moribund/dead.

The mean score for each pig was converted to a "percent morbidity score" by subtracting the corresponding "baseline" value (average for the pre-challenge period [1.00) from the mean post challenge score, then dividing the difference by the adjusted maximum possible score (4.00−1.00=3.00), and multiplying by 100.

Rectal temperature of the pigs was measured on the days 2 through 4 post challenge (not shown in tables). The maximum and mean rectal temperatures during the post-challenge period were determined for each pig. The difference between the maximum rectal temperature during the post-challenge period and the average rectal temperature during the corresponding pre challenge period were calculated for each pig and are shown in Table 1 as maximum rise in temperature.

The body weight of each pig was determined on Days 26 and 41 and recorded in the observation sheets. An Average Daily Gain (ADG) for the post-challenge period was calculated for each pig by subtracting the weight on Day 41 from that on Day 26, and dividing the difference by 15.

The results of the observations are summarized in Table 1.

TABLE 1

Summary of Results from Pigs in Groups I, II, III and IV Post Challenge

| GROUP | NO. OF PIGS PER GROUP | AVG % HEALTHY PIGS PER DAY | AVG % PIGS WITH NORMAL FECAL SCORES PER DAY | MEAN MAXIMUM TEMPERATURE | MEAN RISE IN TEMPERATURE | AVG DAILY GAIN (ADG) |
|---|---|---|---|---|---|---|
| I Vaccinates $5 \times 10^7$ | 17 | 97.5 | 92.0 | 106.4 | 2.8 | 1.08 |
| II Vaccinates $1 \times 10^8$ | 16 | 98.2 | 94.6 | 105.2 | 1.5 | 1.16 |
| III Controls | 19 | 84.2 | 73.7 | 106.0 | 2.3 | 0.97 |
| IV Non Treated | 5 | 100.0 | 100.0 | 104.0 | 0.8 | 1.71 |

These data demonstrate that the challenge level of $1 \times 10^{10}$ CFU was extremely high. However, even under these artificially high exposure conditions, there was a significant (P=<0.0001) difference in morbidity (Average Percent Healthy Pigs Per Day) and diarrhea (P=<0.0001) scores (Average Percent Pigs with Normal Fecal Scores Per Day) between vaccinated pigs in Groups I and II and Control pigs in Group III. Vaccinated pigs from Group II (higher vaccine dose level) had significantly lower (P=<0.05) maximum temperature and maximum rise in temperature when compared with pigs from the Control Group (Group II). No significant differences were observed in Average Daily Gain (ADG) between the vaccinated groups (Groups I and II) and the Control group (Group II). However, a positive trend in ADG emerged among the different treatment groups when compared with pigs from Group IV (Non vaccinated, Non challenged). Group IV pigs had the highest ADG (1.71 lbs.) and Group III had the lowest ADG (0.97 lbs.). The 2 vaccinate groups (Groups I and 11) demonstrated ADGs in between these two values (1.08 and 1.16 lbs., respectively).

Based on the results of this study, vaccination of 3 to 4 week old pigs with *S. cholerasuis* vaccine (Argus SC™) was effective in cross protecting swine against clinical signs of disease caused by a heterologous Salmonella, *S. typhimurium*.

EXAMPLE 2

Since previous publications appear to produce equivocal results when *S. cholerasuis* vaccines were evaluated for the capability to cross protect swine against disease caused by heterologous Salmonella such as *S. typhimurium*, and such studies do not appear to be repeatable, two confirmation studies were conducted to further demonstrate the cross protection afforded by vaccinating 3 to 4 week old pigs with a *S. cholerasuis* vaccine such as Argus SC™ and challenging them with the heterologous serotype, *S. typhimurium*. Additionally these studies were conducted to further demonstrate that mass oral administration via water proportioners is effective.

The vaccine used in both studies was the Bayer Corporation modified live *Salmonella cholerasuis* vaccine (Argus SC™) which has been approved by the Animal Plant Health Inspection Service (APHIS) as an aid in the protection of swine against disease caused by *S. cholerasuis*. The animals were vaccinated as per label recommendations.

Prior to vaccination, 3 week old pigs were ear-tagged and randomly placed into three groups. In each study, Group I pigs were vaccinated orally with a field dose, using water proportioners, at three weeks of age and challenged with virulent *S. typhimurium* and pigs of Group III were not vaccinated or challenged. Group II pigs were not vaccinated but were challenged with virulent *S. typhimurium*. The studies differed in the severity of the challenge ($1 \times 10^{10}$ CFU/pig in Study A and $1 \times 10^6$ CFU/pig in Study B). Also the principle variables recorded during the study were different. Clinical disease was evaluated in Study A while shedding and isolation of *S. typhimurium* in tissues was evaluated in Study B). Pigs were scored for clinical signs of disease for 14 days following challenge in both studies, and isolation for Salmonellae was carried out on daily fecal samples and tissue samples harvested at necropsy in Study B. Table 2 shows a summary of the results.

The pigs were screened and selected for the studies using the same procedure as described in EXAMPLE 1.

The protocol and criteria for these studies were as follows:

Prior to vaccination, water was withdrawn from the pigs for a period of six hours. Three weeks post-vaccination (Day 28), animals of Group I and Group II were challenged orally with a virulent strain of Salmonella typhimurium, P93-482. Prior to challenge, "baseline" values on physical condition, fecal consistency, rectal temperature and body weight were determined for each animal. Before challenge, feed was withdrawn from the pigs for 16 hours. Feed was returned to the pigs after 30 minutes of challenge-exposure. Fourteen days post-challenge, efficacy of the vaccine was assessed by evaluating the physical condition and fecal consistency scores, rectal temperature, and average daily gain (ADG) on various days during the post-challenge Days 29 to 41.

The challenge culture was prepared by removing a frozen vial of *S. typhimurium* and thaw it in a 37° C. water bath. Aliquots (1 mL) of the thawed culture were transferred to two 2 L Erlenmeyer flasks, each of which contained 500 mL of MLB (Modified Luria Bertani) broth (10 g Bacto tryptone, 5 g yeast extract, and 10 g NaCl per liter of deionized water). After 14 to 16 hours of static growth at 37° C.±2° C., the two cultures were combined to obtain a total volume of approximately one-liter. Aliquots (100 mL) were dispensed into sterile bottles and stored in an ice-water bath until administered to the pigs, within one hour of standardization. The challenge material was stored in an ice-water bath until administered to the pigs. A viable bacteria count was done on the challenge culture prior to administration to the pigs. Prior to the challenge, feed was removed from the pens for a period of 18 hours. Each pig was restrained and orally given either $1\times10^{10}$ (Study A) or $1\times10^6$ CFU (Study B) of the *S. typhimurium* challenge strain culture using a plastic syringe.

For sampling and data collection, each pig was assigned to a clinical chart on which clinical observations and sampling were recorded. Mortality was scored throughout the entire study period. Fecal consistency and physical condition were evaluated daily for each pig. Fecal consistency was scored as:

1=Normal, solid or soft-formed
2=Runny, with solid material
3=Watery, with solid material
4=Profuse watery with little or no solid material.

The mean value of stool scores for the 14 day post-challenge observation period was converted to a "percent diarrhea" by subtracting the corresponding "baseline" value (average for the pre-challenge period [1.00]) from the mean post-challenge score. The difference was then divided by the adjusted maximum possible score (4.0−1.0=3.00), and multiplied by 100.

Physical condition (morbidity) of the pigs was scored as:
1=Healthy, active, with a normal hair-coat
2=Slightly active, with a rough hair-coat
3=Inactive/lethargic and/or gaunt irrespective of hair-coat
4=Moribund/dead.

The mean score for each pig was converted to a "percent morbidity score" by subtracting the corresponding "baseline" value (average for the pre-challenge period [1.001] from the mean post challenge score, then dividing the difference by the adjusted maximum possible score (4.00−1.00−3.00), and multiplying by 100. This score is listed in Table 2 as the Average Percent of Healthy Pigs per Day.

Rectal temperature of the pigs was measured on the days 2 through 4 post challenge. The maximum and mean rectal temperatures during the post-challenge period were determined for each pig. The difference between the maximum rectal temperature during the post-challenge period and the average rectal temperature during the corresponding pre challenge period were calculated for each pig and noted as the maximum rise in temperature. The rectal temperature data are not shown in Table 2.

The body weight of each pig was determined on Days 26 and 41 and recorded in the observation sheets. An Average Daily Gain (ADG) for the post-challenge period was calculated for each pig by subtracting the weight on Day 41 from that on Day 26, and dividing the difference by 15.

The fecal culture procedure performed included incubating the fecal swabs in an enrichment media such as Rapport-Vassiliadis broth (Difco, Detroit, Mich.) for 18 to 24 hours at 37° C. and subsequently plating the swabs on Brilliant Green Agar (BGA) plates. The plates were incubated at 37° C. for 24 to 48 hours. Suspected Salmonella (pink) colonies were picked and biochemical tests, namely, Triple Sugar Iron Agar (TSI), Lysine Iron Agar (LIA) and Indole were performed. Also, 'O' typing was performed to determine that the colonies identified were Sero-Group B. The typing was done as per standard procedures using Group B sera obtained from Difco, Detroit, Mich. Shedding of the challenged *S. typhimurium* is summarized in Table 2.

Isolation of *Salmonella typhimurium* From Tissues: The isolation of the challenged organism from the different tissues namely liver, spleen, ileocecal junction (ICJ), mesenteric lymph node (MLN) and tonsil are totaled and listed in Table 2 as Percent Tissues Positive.

TABLE 2

Summary of Results from Pigs in Studies A and B

| STUDY | GROUP | NUMBER OF PIGS PER GROUP | AVG % PIGS WITH NORMAL FECAL SCORES PER DAY | AVG % OF PIGS SHEDDING PER DAY | PERCENT POSITIVE TISSUE | AVG DAILY GAIN (ADG) | DEATHS |
|---|---|---|---|---|---|---|---|
| A | I Vacc | 20 | 96.9 | 96.9 | ND | 1.20 | 1 |
| A | II Cont | 20 | 76.2 | 76.2 | ND | 0.62 | 3 |
| A | III Non Treat | 5 | 100 | 0 | ND | 1.31 | 0 |
| B | I Vacc | 21 | 99.6 | 10.6 | 9.5 | 1.28 | 0 |
| B | II Cont | 19 | 98.0 | 35.9 | 79.0 | 1.18 | 0 |
| B | III Non Treat | 5 | 100 | 1.5 | 0 | 1.00 | 0 |

The results of Studies A and B are shown in Table 2. In Study A, 3 Control pigs died post challenge whereas only 1 vaccinated pig died post challenge. Greater than 96 percent of the vaccinates (Group1) were healthy post challenge as compared with only 76 percent of the Controls (Group II). This was statistically significant at the P=<0.0001 level. The mean rectal temperature of the vaccinated pigs had returned to normal (<103.5°F.) within 48 hours after challenge, but the non-vaccinated pigs remained above normal until day 5 post challenge (not shown in Table). The percent of pigs from Group I that had normal fecal scores (96.5%) were significantly greater (P=<0.01) when compared to the Control pigs from Group II (76.2%). The average daily gain of the vaccinated pigs in Group I (1.2 lb/day) was also significantly (P=<0.05) greater than that of the not-vaccinated pigs in Group II (0.62 lb./day).

Table 2 additionally indicates that in Study B pigs developed only mild transient clinical signs of disease. As a result, group differences in average daily gain, body temperature, and clinical signs were not significant in Study B. However, a significantly greater percent (35.9%) of Control pigs (Group II) shed *S. typhimurium* than in the vaccinated pigs from Group I (10.6%). Significantly more Control pigs (79%) than vaccinated pigs (9.5%) were culture positive for *S. typhimurium* in at least one tissue at necropsy (P=<0.01). More specifically, a significantly higher percent of Control pigs were positive with *S. typhimurium* in the tonsils, mesenteric lymph nodes and ileocecal junction when compared with the vaccinated pigs (P=<0.05).

The conclusion from these studies is that Group I vaccinates had significantly (P=<0.05) lower clinical scores, rectal temperatures and increased average daily gains compared to the non-vaccinated control pigs (Group II) in study A. Vaccinated pigs shed *S. typhimurium* significantly fewer days than the control pigs and *S. typhimurium* was recovered from significantly more tissues from control pigs than from the vaccinated pigs in Study B. Therefore, mass administration of a field dose of *S. cholerasuis* vaccine, especially Argus SC™ to 3 week old pigs significantly reduced shedding of a heterologous Salmonella species, *S. typhimurium*, and significantly reduced the clinical signs of disease following said heterologous challenge.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of immunizing swine to reduce the effects of infection by *Salmonella typhimurium*, comprising administering an effective amount of an avirulent *Salmonella cholerasuis*, wherein the avirulent *Salmonella cholerasuis* has deletions in the cya, crp and cdt genes, whereby said avirulent *Salmonella cholerasuis* does not produce functional adenylate cyclase or functional cyclic AMP receptor protein.

2. The method of claim 1, wherein the avirulent *Salmonella cholerasuis* is administered parenterally or to a mucous membrane.

3. The method of claim 2, wherein the avirulent *Salmonella cholerasuis* is administered orally via drinking water.

* * * * *